(12) United States Patent
Dmytruk et al.

(10) Patent No.: US 8,507,217 B2
(45) Date of Patent: Aug. 13, 2013

(54) **ETHANOL YIELD AND REDUCTION OF BIOMASS ACCUMULATION IN THE RECOMBINANT STRAIN OF *SACCHAROMYCES CEREVISIAE* OVEREXPRESSING ATPASE**

(75) Inventors: Kostyantyn V. Dmytruk, Lviv (UA); Marta V. Semkiv, Lviv (UA); Andriy Sibirny, Lviv (UA)

(73) Assignee: Archer Daniels Midland Company, Decatur, IL (US)

( * ) Notice: Subject to any disclaimer, the term of this patent is extended or adjusted under 35 U.S.C. 154(b) by 85 days.

(21) Appl. No.: 13/376,405

(22) PCT Filed: Jun. 28, 2010

(86) PCT No.: PCT/US2010/040167
§ 371 (c)(1),
(2), (4) Date: Dec. 7, 2011

(87) PCT Pub. No.: WO2010/151866
PCT Pub. Date: Dec. 29, 2010

(65) Prior Publication Data
US 2012/0088290 A1    Apr. 12, 2012

Related U.S. Application Data

(60) Provisional application No. 61/220,814, filed on Jun. 26, 2009.

(51) Int. Cl.
*C12N 15/00* (2006.01)
*C12N 1/20* (2006.01)
*C12N 9/10* (2006.01)
*C12Q 1/48* (2006.01)

(52) U.S. Cl.
USPC ..... 435/15; 435/193; 435/252.3; 435/252.33; 435/252.5

(58) Field of Classification Search
None
See application file for complete search history.

(56) References Cited

U.S. PATENT DOCUMENTS

2003/0233675 A1  12/2003  Cao et al.
2006/0094078 A1   5/2006  Jensen et al.

OTHER PUBLICATIONS

Bai F.W., Anderson W.A., Moo-Young M. (2008) Ethanol fermentation technologies from sugar and starch feedstocks. Biotechnology Advances 26:89-105.
Hahn-Hagerdal B., Karhumaa K.,Jeppsson M., Gorwa-Grauslund M.F.(2007) Metabolic Engineering for Pentose Utilization in *Saccharomyces cerevisiae*. Adv. Biochem. Engin. Biotechnol. 108:147-177.
Handa M., Guidotti G. (1996) Purification and cloning of a soluble ATPdiphosphohydrolase (apyrase) from potato tubers (*Solanum tuberosum*). Biochem. Biophys. Res. Commun. 218: 916-923.
Jeffries T.W. (2005) Ethanol fermentation on the move. Nature 23:40-41.
Jeffries T.W., Jin Y.-S. (2004) Metabolic engineering for improved fermentation of pentoses by yeasts. Appl. Microbiol. Biotechnol. 63: 495-509.
Liberzon A., Shpungin S., Bangio H., Yona E., Katcoff D.J. (1996) Association of yeast SAP1, a novel member of the 'AAA' ATPase family of proteins, with the chromatin protein SIN1. FEBS Lett. 388:5-10.
Plesner L. (1995) Ecto-ATPhases: identities and functions. Int. Rev. Cytol. 158: 141-214.

*Primary Examiner* — Manjunath Rao
*Assistant Examiner* — Jae W Lee
(74) *Attorney, Agent, or Firm* — Mark W. Roberts

(57) ABSTRACT

A new approach for increase of ethanol yield during alcoholic fermentation via decrease of biomass accumulation by using ATP degrading enzymes is described. The part of the *Saccharomyces cerevisiae* SSB1 gene coding for cytosolic ATPase domain of ribosome associated chaperon cloned into expression cassette under control of the glycerol-3-phosphate dehydrogenase gene (GPD1) promoter was introduced into the *S. cerevisiae* BY4742 strain. The recombinant strains were tested for their ability to grow and produce ethanol during glucose anaerobic and aerobic cultivations. Strains overexpressing ATPase domain of SSB1 possessed decreased concentration of intracellular ATP. They accumulated elevated amounts of ethanol and were characterized by decreased biomass accumulation as compared to the wild-type strain under both anaerobic and aerobic conditions. Similarly, the apyrase gene apy from *E. coli* encoding ATP/ADP hydrolyzing phosphatase and ATPase domain of SSB1 gene of *S. cerevisiae* were co-expressed under the control of galactose-inducible GAL1 promoter. The recombinant *S. cerevisiae* strains revealed slight reduction of biomass accumulation, while specific ATPase activity, ethanol accumulation and yield during alcoholic galactose fermentation under semi anaerobic conditions were increased.

15 Claims, 11 Drawing Sheets

A Nt ORF of *S. cerevisiae* SSB2; YDL229W; Chr 4

```
ATGGCTGAAGGTGTTTTCCAAGGTGCTATCGGTATCGATTTAGGTACAACCTACTCTTG
TGTTGCTACTTACGAATCCTCCGTTGAAATTATTGCCAACGAACAAGGTAACAGAGTCA
CCCCATCTTTCGTTGCTTTCACTCCAGAAGAAAGATTGATTGGTGATGCTGCCAAGAAC
CAAGCTGCTTTGAACCCAAGAAACACTGTCTTCGATGCTAAGCGTTTGATTGGTAGAAG
ATTCGACGACGAATCTGTTCAAAAGGACATGAAGACCTGGCCTTTCAAGGTTATCGACG
TCGATGGTAACCCAGTCATCGAAGTCCAATACTTGGAAGAAACCAAGACTTTCTCCCCA
CAAGAAATTTCCGCTATGGTTTTGACCAAGATGAAGGAAATTGCTGAAGCTAAGATTGG
TAAGAAGGTTGAAAAGGCCGTCATTACTGTCCCAGCTTACTTTAACGACGCTCAAAGAC
AAGCTACCAAGGATGCCGGTGCCATTTCTGGTTTGAACGTTTTGCGTATCATCAACGAA
CCTACTGCCGCTGCTATTGCTTACGGTCTAGGTGCTGGTAAGTCCGAAAAGGAAAGACA
TGTTTTGATTTTCGATTTGGGTGGTGGTACTTTCGATGTTTCCTTGTTGCACATTGCTG
GTGGTGTTTACACTGTTAAATCTACTTCCGGTAACACTCACTTGGGTGGTCAAGATTTC
GACACCAACTTGTTGGAACACTTCAAGGCTGAATTCAAGAAGAAGACTGGTTTGGACAT
CTCCGACGATGCCAGAGCTTTGAGAAGATTGAGAACTGCTGCTGAAAGAGCTAAGAGAA
CCTTATCTTCTGTCACTCAAACTACCGTTGAAGTTGACTCTTTGTTTGACGGTGAAGAT
TTCGAATCCTCTTTGACTAGAGCTAGATTTGAAGACTTGAACGCCGCATTGTTCAAGTC
TACTTTGGAACCTGTTGAACAAGTTTTGAAGGATGCTAAGATCTCTAAGTCTCAAATCG
ACGAAGTTGTCTTGGTTGGTGGTTCCACCAGAATTCCAAAGGTCCAAAAGTTGTTGTCT
GACTTCTTTGACGGTAAGCAATTGGAAAAATCTATTAACCCAGATGAAGCTGTTGCTTA
CGGTGCTGCTGTTCAAGGTGCTATCTTGACCGGCCAATCCACATCTGACGAAACCAAGG
ACTTGTTGTTGTTAGATGTTGCTCCATTATCTCTAGGTGTTGGTATGCAAGGTGACATG
TTCGGTATCGTTGTTCCAAGAAACACTACTGTTCCAACCATCAAGAGAAGAACCTTTAC
TACATGTGCTGACAACCAAACCACCGTTCAATTCCCAGTCTACCAAGGTGAACGTGTTA
ACTGTAAAGAAAACACTTTGTTGGGTGAATTCGACTTGAAGAACATCCCAATGATGCCA
GCTGGTGAACCAGTCTTGGAAGCTATCTTCGAAGTTGATGCTAACGGTATCTTGAAGGT
TACTGCCGTCGAAAAGTCTACCGGTAAGTCTTCTAACATCACTATCTCTAACGCTGTTG
GTAGATTGTCTTCTGAAGAAATTGAAAAGATGGTTAACCAAGCTGAAGAGTTCAAGGCT
GCCGATGAAGCTTTTGCCAAGAAGCACGAAGCTAGACAAAGATTGGAATCCTACGTTGC
CTCCATCGAACAAACTGTCACTGACCCAGTCTTGTCTTCTAAATTGAAGAGAGGTTCCA
AGTCCAAGATTGAAGCTGCTTTGTCCGATGCTTTGGCTGCTTTGCAAATCGAAGACCCA
TCTGCTGATGAATTGAGAAAGGCTGAAGTTGGTTTGAAGAGAGTTGTCACCAAGGCCAT
GTCTTCTCGTTAA
```

Fig. 2A

B Nt ORF of nSSB2

ATGGCTGAAGGTGTTTTCCAAGGTGCTATCGGTATCGATTTAGGTACAACCTACTCTTG
TGTTGCTACTTACGAATCCTCCGTTGAAATTATTGCCAACGAACAAGGTAACAGAGTCA
CCCCATCTTTCGTTGCTTTCACTCCAGAAGAAAGATTGATTGGTGATGCTGCCAAGAAC
CAAGCTGCTTTGAACCCAAGAAACACTGTCTTCGATGCTAAGCGTTTGATTGGTAGAAG
ATTCGACGACGAATCTGTTCAAAAGGACATGAAGACCTGGCCTTTCAAGGTTATCGACG
TCGATGGTAACCCAGTCATCGAAGTCCAATACTTGGAAGAAACCAAGACTTTCTCCCCA
CAAGAAATTTCCGCTATGGTTTTGACCAAGATGAAGGAAATTGCTGAAGCTAAGATTGG
TAAGAAGGTTGAAAAGGCCGTCATTACTGTCCCAGCTTACTTTAACGACGCTCAAAGAC
AAGCTACCAAGGATGCCGGTGCCATTTCTGGTTTGAACGTTTTGCGTATCATCAACGAA
CCTACTGCCGCTGCTATTGCTTACGGTCTAGGTGCTGGTAAGTCCGAAAAGGAAAGACA
TGTTTTGATTTTCGATTTGGGTGGTGGTACTTTCGATGTTTCCTTGTTGCACATTGCTG
GTGGTGTTTACACTGTTAAATCTACTTCCGGTAACACTCACTTGGGTGGTCAAGATTTC
GACACCAACTTGTTGGAACACTTCAAGGCTGAATTCAAGAAGAAGACTGGTTTGGACAT
CTCCGACGATGCCAGAGCTTTGAGAAGATTGAGAACTGCTGCTGAAAGAGCTAAGAGAA
CCTTATCTTCTGTCACTCAAACTACCGTTGAAGTTGACTCTTTGTTTGACGGTGAAGAT
TTCGAATCCTCTTTGACTAGAGCTAGATTTGAAGACTTGAACGCCGCATTGTTCAAGTC
TACTTTGGAACCTGTTGAACAAGTTTTGAAGGATGCTAAGATCTCTAAGTCTCAAATCG
ACGAAGTTGTCTTGGTTGGTGGTTCCACCAGAATTCCAAAGGTCCAAAAGTTGTTGTCT
GACTTCTTTGACGGTAAGCAATTGGAAAAATCTATTAACCCAGATGAAGCTGTTGCTTA
CGGTGCTGCTGTTCAAGGTGCTATCTTGACCGGCCAATCCACATCTGACGAAACCAAGG
ACTTGTTGTTGTTAGATGTTGCTCCATTATCTCTAGGTGTTGGTATGCAAGGTTGA

Fig. 2B

C Pep. ORF of nSSB2

MAEGVFQGAIGIDLGTTYSCVATYESSVEIIANEQGNRVTPSFVAFTPEERLIGDAAKNQ
AALNPRNTVFDAKRLIGRRFDDESVQKDMKTWPFKVIDVDGNPVIEVQYLEETKTFSPQE
ISAMVLTKMKEIAEAKIGKKVEKAVITVPAYFNDAQRQATKDAGAISGLNVLRIINEPTA
AAIAYGLGAGKSEKERHVLIFDLGGGTFDVSLLHIAGGVYTVKSTSGNTHLGGQDFDTNL
LEHFKAEFKKKTGLDISDDARALRRLRTAAERAKRTLSSVTQTTVEVDSLFDGEDFESSL
TRARFEDLNAALFKSTLEPVEQVLKDAKISKSQIDEVVLVGGSTRIPKVQKLLSDFFDGK
QLEKSINPDEAVAYGAAVQGAILTGQSTSDETKDLLLLDVAPLSLGVGMQG*

ATGAAAACCAAAAACTTTCTTCTTTTTTGTATTGCTACAAATATGATTTTTATCCCCTCAGCAA
ATGCTCTGAAGGCAGAAGGTTTTCTCACTCAACAAACTTCACCAGACAGTTTGTCAATACTTCC
GCCGCCTCCGGCAGAGGATTCAGTAGTATTTCAGGCTGACAAAGCTCATTATGAATTCGGCCGC
TCGCTCCGGGATGCTAATCGTGTACGTCTCGCTAGCGAAGATGCATACTACGAGAATTTTGGTC
TTGCATTTTCAGATGCTTATGGCATGGATATTTCAAGGGAAAATACCCCAATCTTATATCAGTT
GTTAACACAAGTACTACAGGATAGCCATGATTACGCCGTGCGTAACGCCAAAGAATATTATAAA
AGAGTTCGTCCATTCGTTATTTATAAAGACGCAACCTGTACACCTGATAAAGATGAGAAAATGG
CTATCACTGGCTCTTATCCCTCTGGTCATGCATCCTTTGGTTGGGCAGTAGCACTGATACTTGC
GGAGATTAATCCTCAACGTAAAGCGGAAATACTTCGACGTGGATATGAGTTTGGAGAAAGTCGG
GTCATCTGCGGTGCGCATTGGCAAAGCGATGTAGAGGCTGGGCGTTTAATGGGAGCATCGGTTG
TTGCAGTACTTCATAATACACCTGAATTTACCAAAAGCCTTAGCGAAGCCAAAAAAGAGTTTGA
AGAATTAAATACTCCTACCAATGAACTGACCCCATAA

ATGCTGAAGGCAGAAGGTTTTCTCACTCAACAAACTTCACCAGACAGTTTGTCAATACTTCCGC
CGCCTCCGGCAGAGGATTCAGTAGTATTTCAGGCTGACAAAGCTCATTATGAATTCGGCCGCTC
GCTCCGGGATGCTAATCGTGTACGTCTCGCTAGCGAAGATGCATACTACGAGAATTTTGGTCTT
GCATTTTCAGATGCTTATGGCATGGATATTTCAAGGGAAAATACCCCAATCTTATATCAGTTGT
TAACACAAGTACTACAGGATAGCCATGATTACGCCGTGCGTAACGCCAAAGAATATTATAAAAG
AGTTCGTCCATTCGTTATTTATAAAGACGCAACCTGTACACCTGATAAAGATGAGAAAATGGCT
ATCACTGGCTCTTATCCCTCTGGTCATGCATCCTTTGGTTGGGCAGTAGCACTGATACTTGCGG
AGATTAATCCTCAACGTAAAGCGGAAATACTTCGACGTGGATATGAGTTTGGAGAAAGTCGGGT
CATCTGCGGTGCGCATTGGCAAAGCGATGTAGAGGCTGGGCGTTTAATGGGAGCATCGGTTGTT
GCAGTACTTCATAATACACCTGAATTTACCAAAAGCCTTAGCGAAGCCAAAAAAGAGTTTGAAG
AATTAAATACTCCTACCAATGAACTGACCCCATAA

MLKAEGFLTQQTSPDSLSILPPPPAEDSVVFQADKAHYEFGRSLRDANRVRLASEDAYYE
NFGLAFSDAYGMDISRENTPILYQLLTQVLQDSHDYAVRNAKEYYKRVRPFVIYKDATCT
PDKDEKMAITGSYPSGHASFGWAVALILAEINPQRKAEILRRGYEFGESRVICGAHWQSD
VEAGRLMGASVVAVLHNTPEFTKSLSEAKKEFEELNTPTNELTP

Fig. 10C

SEQUENCE LISTING

<160> NUMBER OF SEQ ID NOS: 16

<210> SEQ ID NO 1
<211> LENGTH: 1842
<212> TYPE: DNA
<213> ORGANISM: Saccharomyces cerevisiae

<400> SEQUENCE: 1

| | | | | | |
|---|---|---|---|---|---|
| atggctgaag | gtgttttcca | aggtgctatc | ggtatcgatt | taggtacaac | ctactcttgt | 60 |
| gttgctactt | acgaatcctc | cgttgaaatt | attgccaacg | aacaaggtaa | cagagtcacc | 120 |
| ccatctttcg | ttgctttcac | tccagaagaa | agattgattg | gtgatgctgc | caagaaccaa | 180 |
| gctgctttga | acccaagaaa | cactgtcttc | gatgctaagc | gtttgattgg | tagaagattc | 240 |
| gacgacgaat | ctgttcaaaa | ggacatgaag | acctggcctt | tcaaggttat | cgacgtcgat | 300 |
| ggtaacccag | tcatcgaagt | ccaatacttg | gaagaaacca | agactttctc | cccacaagaa | 360 |
| atttccgcta | tggttttgac | caagatgaag | gaaattgctg | aagctaagat | tggtaagaag | 420 |
| gttgaaaagg | ccgtcattac | tgtcccagct | tactttaacg | acgctcaaag | acaagctacc | 480 |
| aaggatgccg | gtgccatttc | tggtttgaac | gttttgcgta | tcatcaacga | acctactgcc | 540 |
| gctgctattg | cttacggtct | aggtgctggt | aagtccgaaa | aggaaagaca | tgttttgatt | 600 |
| ttcgatttgg | gtggtggtac | tttcgatgtt | tccttgttgc | acattgctgg | tggtgtttac | 660 |
| actgttaaat | ctacttccgg | taacactcac | ttgggtggtc | aagatttcga | caccaacttg | 720 |
| ttggaacact | tcaaggctga | attcaagaag | aagactggtt | tggacatctc | cgacgatgcc | 780 |
| agagctttga | agaagattgag | aactgctgct | gaaagagcta | agagaacctt | atcttctgtc | 840 |
| actcaaacta | ccgttgaagt | tgactctttg | tttgacggtg | aagatttcga | atcctctttg | 900 |
| actagagcta | gatttgaaga | cttgaacgcc | gcattgttca | agtctacttt | ggaacctgtt | 960 |
| gaacaagttt | tgaaggatgc | taagatctct | aagtctcaaa | tcgacgaagt | tgtcttggtt | 1020 |
| ggtggttcca | ccagaattcc | aaaggtccaa | aagttgtttgt | ctgacttctt | tgacggtaag | 1080 |
| caattggaaa | aatctattaa | cccagatgaa | gctgttgctt | acggtgctgc | tgttcaaggt | 1140 |
| gctatcttga | ccggccaatc | cacatctgac | gaaaccaagg | acttgttgtt | gttagatgtt | 1200 |
| gctccattat | ctctaggtgt | tggtatgcaa | ggtgacatgt | tcggtatcgt | tgttccaaga | 1260 |
| aacactactg | ttccaaccat | caagagaaga | acctttacta | catgtgctga | caaccaaacc | 1320 |
| accgttcaat | tcccagtcta | ccaaggtgaa | cgtgttaact | gtaaagaaaa | cactttgttg | 1380 |
| ggtgaattcg | acttgaagaa | catcccaatg | atgccagctg | gtgaaccagt | cttggaagct | 1440 |
| atcttcgaag | ttgatgctaa | cggtatcttg | aaggttactc | cgtcgaaaa | gtctaccggt | 1500 |
| aagtcttcta | acatcactat | ctctaacgct | gttggtagat | tgtcttctga | agaaattgaa | 1560 |
| aagatggtta | accaagctga | agagttcaag | gctgccgatg | aagcttttgc | caagaagcac | 1620 |
| gaagctagac | aaagattgga | atcctacgtt | gcctccatcg | aacaaactgt | cactgaccca | 1680 |
| gtcttgtctt | ctaaattgaa | gagaggttcc | aagtccaaga | ttgaagctgc | tttgtccgat | 1740 |
| gctttggctg | ctttgcaaat | cgaagaccca | tctgctgatg | aattgagaaa | ggctgaagtt | 1800 |

```
ggtttgaaga gagttgtcac caaggccatg tcttctcgtt aa                       1842

<210> SEQ ID NO 2
<211> LENGTH: 1236
<212> TYPE: DNA
<213> ORGANISM: Saccharomyces cerevisiae

<400> SEQUENCE: 2
atggctgaag gtgttttcca aggtgctatc ggtatcgatt taggtacaac ctactcttgt     60
gttgctactt acgaatcctc cgttgaaatt attgccaacg aacaaggtaa cagagtcacc    120
ccatctttcg ttgctttcac tccagaagaa agattgattg gtgatgctgc caagaaccaa    180
gctgctttga acccaagaaa cactgtcttc gatgctaagc gtttgattgg tagaagattc    240
gacgacgaat ctgttcaaaa ggacatgaag acctggcctt tcaaggttat cgacgtcgat    300
ggtaacccag tcatcgaagt ccaatacttg aagaaaccaa gactttctc cccacaagaa    360 atttccgcta tggttttgac caagatgaag gaaattgctg aagctaagat tggtaagaag    420
gttgaaaagg ccgtcattac tgtcccagct tactttaacg acgctcaaag acaagctacc    480
aaggatgccg gtgccatttc tggtttgaac gttttgcgta tcatcaacga acctactgcc    540
gctgctattg cttacggtct aggtgctggt aagtccgaaa aggaaagaca tgttttgatt    600
ttcgatttgg gtggtggtac tttcgatgtt tccttgttgc acattgctgg tggtgtttac    660
actgttaaat ctacttccgg taacactcac ttgggtggtc aagatttcga caccaacttg    720
ttggaacact tcaaggctga attcaagaag aagactggtt ggacatctc cgacgatgcc    780 agagctttga agagttgag aactgctgct gaaagagcta agagaacctt atcttctgtc    840
actcaaacta ccgttgaagt tgactctttg tttgacggtg aagatttcga atcctcttg    900 actagagcta gatttgaaga cttgaacgcc gcattgttca gtctactttt ggaacctgtt    960
gaacaagttt tgaaggatgc taagatctct aagtctcaaa tcgacgaagt tgtcttggtt   1020
ggtggttcca ccagaattcc aaaggtccaa agttgttgt ctgacttctt tgacggtaag   1080
caattggaaa aatctattaa cccagatgaa gctgttgctt acggtgctgc tgttcaaggt   1140
gctatcttga ccggccaatc cacatctgac gaaaccaagg acttgttgtt gttagatgtt   1200
gctccattat ctctaggtgt tggtatgcaa ggttga                             1236

<210> SEQ ID NO 3
<211> LENGTH: 411
<212> TYPE: PRT
<213> ORGANISM: Saccharomyces cerevisiae

<400> SEQUENCE: 3

Met Ala Glu Gly Val Phe Gln Gly Ala Ile Gly Ile Asp Leu Gly Thr
1               5                   10                  15

Thr Tyr Ser Cys Val Ala Thr Tyr Glu Ser Ser Val Glu Ile Ile Ala
                20                  25                  30

Asn Glu Gln Gly Asn Arg Val Thr Pro Ser Phe Val Ala Phe Thr Pro
            35                  40                  45

Glu Glu Arg Leu Ile Gly Asp Ala Ala Lys Asn Gln Ala Ala Leu Asn
        50                  55                  60

Pro Arg Asn Thr Val Phe Asp Ala Lys Arg Leu Ile Gly Arg Arg Phe
65                  70                  75                  80

Asp Asp Glu Ser Val Gln Lys Asp Met Lys Thr Trp Pro Phe Lys Val
                85                  90                  95

Ile Asp Val Asp Gly Asn Pro Val Ile Glu Val Gln Tyr Leu Glu Glu
```

```
            100                 105                 110
Thr Lys Thr Phe Ser Pro Gln Glu Ile Ser Ala Met Val Leu Thr Lys
        115                 120                 125

Met Lys Glu Ile Ala Glu Ala Lys Ile Gly Lys Val Glu Lys Ala
    130                 135                 140

Val Ile Thr Val Pro Ala Tyr Phe Asn Asp Ala Gln Arg Gln Ala Thr
145                 150                 155                 160

Lys Asp Ala Gly Ala Ile Ser Gly Leu Asn Val Leu Arg Ile Ile Asn
                165                 170                 175

Glu Pro Thr Ala Ala Ala Ile Ala Tyr Gly Leu Gly Ala Gly Lys Ser
            180                 185                 190

Glu Lys Glu Arg His Val Leu Ile Phe Asp Leu Gly Gly Gly Thr Phe
        195                 200                 205

Asp Val Ser Leu Leu His Ile Ala Gly Gly Val Tyr Thr Val Lys Ser
    210                 215                 220

Thr Ser Gly Asn Thr His Leu Gly Gly Gln Asp Phe Asp Thr Asn Leu
225                 230                 235                 240

Leu Glu His Phe Lys Ala Glu Phe Lys Lys Lys Thr Gly Leu Asp Ile
                245                 250                 255

Ser Asp Asp Ala Arg Ala Leu Arg Arg Leu Arg Thr Ala Ala Glu Arg
            260                 265                 270

Ala Lys Arg Thr Leu Ser Ser Val Thr Gln Thr Thr Val Glu Val Asp
        275                 280                 285

Ser Leu Phe Asp Gly Glu Asp Phe Glu Ser Ser Leu Thr Arg Ala Arg
    290                 295                 300

Phe Glu Asp Leu Asn Ala Ala Leu Phe Lys Ser Thr Leu Glu Pro Val
305                 310                 315                 320

Glu Gln Val Leu Lys Asp Ala Lys Ile Ser Lys Ser Gln Ile Asp Glu
                325                 330                 335

Val Val Leu Val Gly Gly Ser Thr Arg Ile Pro Lys Val Gln Lys Leu
            340                 345                 350

Leu Ser Asp Phe Phe Asp Gly Lys Gln Leu Glu Lys Ser Ile Asn Pro
        355                 360                 365

Asp Glu Ala Val Ala Tyr Gly Ala Ala Val Gln Gly Ala Ile Leu Thr
    370                 375                 380

Gly Gln Ser Thr Ser Asp Glu Thr Lys Asp Leu Leu Leu Leu Asp Val
385                 390                 395                 400

Ala Pro Leu Ser Leu Gly Val Gly Met Gln Gly
                405                 410

<210> SEQ ID NO 4
<211> LENGTH: 741
<212> TYPE: DNA
<213> ORGANISM: Escherichia coli

<400> SEQUENCE: 4
atgaaaacca aaactttct tcttttttgt attgctacaa atatgatttt tatcccctca      60
gcaaatgctc tgaaggcaga aggttttctc actcaacaaa cttcaccaga cagtttgtca     120
atacttccgc cgcctccggc agaggattca gtagtatttc aggctgacaa agctcattat     180
gaattcggcc gctcgctccg ggatgctaat cgtgtacgtc tcgctagcga agatgcatac     240
tacgagaatt ttggtcttgc attttcagat gcttatggca tggatatttc aagggaaaat     300
accccaatct tatatcagtt gttaacacaa gtactacagg atagccatga ttacgccgtg     360
cgtaacgcca agaatattat aaaagagtt cgtccattcg ttatttataa agacgcaacc     420
```

-continued

```
tgtacacctg ataaagatga gaaaatggct atcactggct cttatccctc tggtcatgca    480
tcctttggtt gggcagtagc actgatactt gcggagatta atcctcaacg taaagcggaa    540
atacttcgac gtggatatga gtttggagaa agtcgggtca tctgcggtgc cattggcaa     600 agcgatgtag aggctgggcg tttaatggga gcatcggttg ttgcagtact tcataataca    660
cctgaattta ccaaaagcct tagcgaagcc aaaaaagagt ttgaagaatt aaatactcct    720
accaatgaac tgaccccata a                                              741
```

<210> SEQ ID NO 5
<211> LENGTH: 675
<212> TYPE: DNA
<213> ORGANISM: Escherichia coli

<400> SEQUENCE: 5

```
atgctgaagg cagaaggttt tctcactcaa caaacttcac cagacagttt gtcaatactt     60
ccgccgcctc cggcagagga ttcagtagta tttcaggctg acaaagctca ttatgaattc    120
ggccgctcgc tccgggatgc taatcgtgta cgtctcgcta gcgaagatgc atactacgag    180
aattttggtc ttgcattttc agatgcttat ggcatggata tttcaaggga aaatacccca    240
atcttatatc agttgttaac acaagtacta caggatagcc atgattacgc cgtgcgtaac    300
gccaaagaat attataaaag agtcgtccca ttcgttattt ataaagacgc aacctgtaca    360
cctgataaag atgagaaaat ggctatcact ggctcttatc cctctggtca tgcatccttt    420
ggttgggcag tagcactgat acttgcggag attaatcctc aacgtaaagc ggaaatactt    480
cgacgtggat atgagtttgg agaaagtcgg gtcatctgcg gtgcgcattg gcaaagcgat    540
gtagaggctg gccgtttaat gggagcatcg gttgttgcag tacttcataa tacacctgaa    600
tttaccaaaa gccttagcga agccaaaaaa gagtttgaag aattaaatac tcctaccaat    660
gaactgaccc cataa                                                     675
```

<210> SEQ ID NO 6
<211> LENGTH: 224
<212> TYPE: PRT
<213> ORGANISM: Escherichia coli

<400> SEQUENCE: 6

```
Met Leu Lys Ala Glu Gly Phe Leu Thr Gln Gln Thr Ser Pro Asp Ser
1               5                   10                  15

Leu Ser Ile Leu Pro Pro Pro Ala Glu Asp Ser Val Val Phe Gln
            20                  25                  30

Ala Asp Lys Ala His Tyr Glu Phe Gly Arg Ser Leu Arg Asp Ala Asn
        35                  40                  45

Arg Val Arg Leu Ala Ser Glu Asp Ala Tyr Tyr Glu Asn Phe Gly Leu
    50                  55                  60

Ala Phe Ser Asp Ala Tyr Gly Met Asp Ile Ser Arg Glu Asn Thr Pro
65                  70                  75                  80

Ile Leu Tyr Gln Leu Leu Thr Gln Val Leu Gln Asp Ser His Asp Tyr
                85                  90                  95

Ala Val Arg Asn Ala Lys Glu Tyr Tyr Lys Arg Val Arg Pro Phe Val
            100                 105                 110

Ile Tyr Lys Asp Ala Thr Cys Thr Pro Asp Lys Asp Glu Lys Met Ala
        115                 120                 125

Ile Thr Gly Ser Tyr Pro Ser Gly His Ala Ser Phe Gly Trp Ala Val
    130                 135                 140
```

-continued

Ala Leu Ile Leu Ala Glu Ile Asn Pro Gln Arg Lys Ala Glu Ile Leu
145                 150                 155                 160

Arg Arg Gly Tyr Glu Phe Gly Glu Ser Arg Val Ile Cys Gly Ala His
                165                 170                 175

Trp Gln Ser Asp Val Glu Ala Gly Arg Leu Met Gly Ala Ser Val Val
            180                 185                 190

Ala Val Leu His Asn Thr Pro Glu Phe Thr Lys Ser Leu Ser Glu Ala
        195                 200                 205

Lys Lys Glu Phe Glu Glu Leu Asn Thr Pro Thr Asn Glu Leu Thr Pro
    210                 215                 220

<210> SEQ ID NO 7
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 7
tgagctcagc gtgtagacgt agtataac                                        28

<210> SEQ ID NO 8
<211> LENGTH: 29
<212> TYPE: DNA
<213> ORGANISM: Artificial
<220> FEATURE:
<223> OTHER INFORMATION: Primer for amplification

<400> SEQUENCE: 8
tctagatctc tatcagcagc agcagacag                                       29

<210> SEQ ID NO 9
<211> LENGTH: 28
<212> TYPE: DNA
<213> ORGANISM: Artificial
<220> FEATURE:
<223> OTHER INFORMATION: Primer for amplification

<400> SEQUENCE: 9
atcccgggaa gcctgtgagt aaacaggc                                        28

<210> SEQ ID NO 10
<211> LENGTH: 28
<212> TYPE: DNA
<213> ORGANISM: Artificial
<220> FEATURE:
<223> OTHER INFORMATION: Primer for amplification

<400> SEQUENCE: 10
tagtcgactg ttacatgcgt acacgcgt                                        28

<210> SEQ ID NO 11
<211> LENGTH: 31
<212> TYPE: DNA
<213> ORGANISM: Artificial
<220> FEATURE:
<223> OTHER INFORMATION: Primer for amplification

<400> SEQUENCE: 11
atctagatcc tcattaacaa tggctgaagg t                                    31

<210> SEQ ID NO 12
<211> LENGTH: 32
<212> TYPE: DNA
<213> ORGANISM: Artificial

```
<220> FEATURE:
<223> OTHER INFORMATION: Primer for amplification

<400> SEQUENCE: 12
atcccgggaa ttcaaccttg cataccaaca cc                                    32

<210> SEQ ID NO 13
<211> LENGTH: 33
<212> TYPE: DNA
<213> ORGANISM: Artificial
<220> FEATURE:
<223> OTHER INFORMATION: Primer for amplification

<400> SEQUENCE: 13
cgcggatcca tgctgaaggc agaaggtttt ctc                                   33

<210> SEQ ID NO 14
<211> LENGTH: 47
<212> TYPE: DNA
<213> ORGANISM: Artificial
<220> FEATURE:
<223> OTHER INFORMATION: Primer for amplification

<400> SEQUENCE: 14
tttgcggccg cttatggggt cagttcattg gtaggagtat ttaattc                    47

<210> SEQ ID NO 15
<211> LENGTH: 34
<212> TYPE: DNA
<213> ORGANISM: Artificial
<220> FEATURE:
<223> OTHER INFORMATION: Primer for amplification

<400> SEQUENCE: 15
cgcggatcca tggctgaagg tgttttccaa ggtg                                  34

<210> SEQ ID NO 16
<211> LENGTH: 31
<212> TYPE: DNA
<213> ORGANISM: Artificial
<220> FEATURE:
<223> OTHER INFORMATION: Primer for amplification

<400> SEQUENCE: 16
tttgcggccg ctcaaccttg cataccaaca c                                     31
```

ETHANOL YIELD AND REDUCTION OF BIOMASS ACCUMULATION IN THE RECOMBINANT STRAIN OF *SACCHAROMYCES CEREVISIAE* OVEREXPRESSING ATPASE

CROSS REFERENCE TO RELATED APPLICATION

This application claims priority to international application No: PCT/US10/40167 filed Jun. 28, 2010 and to U.S. provisional application No. 61/220,814 filed Jun. 26, 2009.

TECHNICAL FIELD

The present disclosure relates to modified yeast for enhanced production of ethanol by fermentation, more particularly to yeast modified to produce less ATP when grown under conditions to produce ethanol, and still more particularly to overexpression of a cytosolic ATPase activity in *S. cerevisiae* with or without co-expression of an apyrase activity, both resulting in a simultaneous decrease of ATP in the cell, a decrease in cellular biomass accumulation and an increase in ethanol production under anaerobic and aerobic growth conditions for producing ethanol.

BACKGROUND OF THE INVENTION

Alcoholic fermentation is an anaerobic catabolism of glucose and some other hexoses leading to production of extracellular ethanol and $CO_2$. During the catabolic process, ATP is formed and used for anabolic purposes resulting in cell growth and propagation (Bai et al., 2008). The efficiency of ATP synthesis during anaerobic glucose catabolism is quite low, varying, depending on the particular glucose catabolic pathway, from one mole of ATP (Entner-Doudoroff or ED pathway) to two moles of ATP (Embden-Meyerhof-Parnas or EMP pathway) per mole of consumed glucose, in contrast to aerobic catabolism where one mole of glucose results in production of 36 moles of ATP. Correspondingly, the efficiency of glucose conversion to cellular biomass by cell division and growth is lowest during anaerobic ED catabolic pathway and is highest during aerobic glucose oxidation.

On a volume basis, alcoholic fermentation represents one of the largest fields of industrial biotechnology being used for production of traditional alcoholic beverages (wine, beer, strong alcoholic beverages, etc.) as well as industrial and fuel ethanol. Due to economic and environmental reasons, an exponential growth in production of fuel ethanol occurred during the last decade (Schubert, 2006). Although lignocellulose is considered to be the most promising feedstock for production of fuel ethanol in the future, current industrial production of fuel ethanol is based on fermentation of traditional feedstocks such as sucrose (of sugarcane or sugar beet) and glucose obtained from starchy materials (corn, potatoes etc). The only organism currently used for industrial ethanol production is the baker's yeast *Saccharomyces cerevisiae*. This yeast catabolizes glucose through the glycolytic EMP pathway yielding 2 moles of ATP per mole of consumed glucose. Because the metabolic efficiency of this pathway is low, the maximal biomass yield is only about 7% while the ethanol yield from glucose is between 90 and 93% of the theoretical value (Ingledew, 1999). Nonetheless, at the industrial scale, 7% of biomass is a huge amount of by-product, which although possessing some economic value as an animal feed ingredient, still significantly lowers the potential yield of the primary product, i.e., of ethanol that could theoretically be obtained. As annual ethanol production reaches over 50 billion liters, an increase in ethanol yield as little as 1-2% could provide additional hundreds of millions to a billion liters of ethanol and significantly improve economic parameters of ethanol production.

In contrast to *S. cerevisiae*, the bacterium *Zymomonas mobilis* ferments glucose through the ED pathway, which gives only 1 mole of ATP per mole of glucose, and directs only 3% of glucose to biomass achieving ethanol yield up to 97% of the theoretically possible value (Sprenger, 1996). Furthermore, *Z. mobilis* has another important advantage: it is much faster at fermenting glucose to ethanol compared to *S. cerevisiae* (Sprenger, 1996, Panesar et al., 2006), however, this peculiarity mostly is explained by a faster rate of sugar uptake and subsequent catabolism rather than a lower ATP yield. Attempts to substitute *S. cerevisiae* by *Z. mobilis* for production of industrial ethanol were considered as a possible way to increase the ethanol yield by ferementation some 3-4%, which would translate into a hundred million liters in world scale annually. However, *Z. mobilis* is not free of serious drawbacks which hamper its industrial use now and in near future. They are: (i) it has a very narrow substrate range (sucrose is hardly fermented, and then with low yields), (ii) it has natural auxotrophy for lysine, methionine and some vitamins, (iii) it has non-GRAS status, which prevents use of the biomass by-product as a feed additive (Jeffries, 2005; Bai et al., 2008). Moreover as the main workhorse for ethanol production, the technology of yeast cells for alcoholic fermentation is well developed whereas the fermentation technology for bacterial cells like *Z. mobilis* is far less developed.

One prior art approach attempted substitution of the essential components of the EMP pathway in yeast with those of the ED pathway from bacteria possessing genes of this pathway such as *Z. mobilis*. This approach included expression of ED dehydratase and ED aldolase genes edd and eda in a phosphofructokinase deficient mutant of *S. cerevisiae* (Lancashire et al., 1998). The resulting yeast transformants grew and fermented glucose to ethanol, though the activities of ED dehydratase and ED aldolase were not measured. Apparently this approach did not see further development in the scientific literature. One explanation may be that quite often prokaryotic enzymes display low or no activity in *S. cerevisiae* hosts (Hahn-Hagerdal et al., 2007), probably due to improper folding or instability. In addition, there may be difficulties in NADP regeneration in yeast engineered to use the ED pathway because NADPH produced by glucose-6-phosphate dehydrogenase should be reoxidized by the alcohol dehydrogenase reaction. However, the major alcohol dehydrogenases in *S. cerevisiae* use NADH but not NADPH and yeast do not possess NADH/NADPH transhydrogenase (Lescovac et al., 2002; Jeffries and Jin, 2004).

Therefore, there is a continuing need in the art to find ways to enhance ethanol production with yeast such as *S. cerevisiae*. The present invention provides methods for simultaneously decreasing biomasss accumulation and increasing ethanol production by yeast by manipulation of ATP levels in the yeast.

SUMMARY OF THE INVENTION

The present disclosure teaches ways of increasing ethanol production by lowering the level of ATP in the cytosol of yeast which mimics the effects of the ED pathway of bacteria without need to express ED genes. The result has several distinguishable but related aspects and embodiments.

One aspect is yeast strains. These embodiments include two types of yeast strains that include a recombinant nucleic acid that encodes an ATP degrading protein that lowers ATP levels in the cytosol of the yeast characterized in that the recombinant nucleic includes a promoter operable operably linked to overexpress a nucleic acid encoding the ATP degrading protein. In one aspect, the ATP degrading protein is a cytosol soluble ATPase. In another aspect the ATP degrading protein is an apyrase.

In one embodiment, the yeast strain contains a recombinant nucleic acid that only encodes the cytosol soluble ATPase. One particular embodiment of a cytosol soluble ATPase is a soluble N-terminal portion of a S. cerevisiae.SSB2 protein. An exemplary embodiment of a soluble N-terminal portion of the S. cerevisiae.SSB2 protein is according to SEQ. ID NO: 3, and in a particular case, the nucleic acid encoding the N-terminal portion of the S. cerevisiae.SSB2 protein is according to SEQ. ID NO: 2.

In another embodiment the yeast strain contains a recombinant nucleic acid that only encodes the apyrase. In one particular case, the apyrase is an E. coli apyrase. An exemplary embodiment of the E. coli apyrase is according to SEQ. ID NO: 6 and one exemplary the nucleic acid encoding the apyrase is according to SEQ. ID NO: 5.

In certain embodiments, both the cytosol soluble ATPase and the apyrase are over expressed. Exemplary and particular embodiments include combinations of the same sequences motioned above.

While the soluble ATPase and/or apyrase may be expressed in any yeast, a preferred embodiment is where the yeast strain is S. cerevisiae.

In another aspect, there are provided methods of enhancing ethanol production by yeast fermentation using any of the foregoing yeast strains. The methods include, growing the recombinant yeast strain overexpressing the ATP degrading protein on a carbohydrate source under conditions where the carbohydrate source is fermented to make ethanol. The amount of ethanol made in by the recombinant yeast strain under the growth conditions is greater than the amount of ethanol made in a parent of the recombinant yeast strain that lacks the recombinant nucleic acid overexpressing the ATP degrading protein.

Embodiments of these method of enhancing ethanol production includes growing the yeast under aerobic conditions, or anaerobic conditions or growing the yeast under aerobic conditions for a first period of time and then growing the yeast under anaerobic conditions for a second period of time and where the enhanced ethanol production occurs under the anaerobic growth conditions.

Another aspect is the recombinant nucleic acids used in the yeast strains above. Such recombinant nucleic acids comprising a promoter element operable to overexpress a nucleic acid in yeast operably linked to a nucleic acid encoding at least one enzyme selected from the group consisting of a cytosol soluble ATPase and an apyrase. Exemplary and particular embodiments of this aspect include any and all of the above mentioned sequences.

BRIEF DESCRIPTION OF THE DRAWINGS

Shows 1 linearized maps of: A. the plasmid pGPD1P carrying the GPD1 promoter and CYC1 terminator (the expression cassette). B, the plasmid pUSgpdp-zeo carrying NSSB1 under the GPD1 promoter and terminated with the CYC1 terminator; ZeoR, the ble gene conferring resistance to zeocin. C, the plasmid pYES2-apy carrying apy gene under the GPD1 promoter and terminated with the CYC1 terminator. D, the plasmid pYES2-NSSB carrying NSSB1 gene under the GPD1 promoter and terminated with the CYC1 terminator; URA3 auxotrophy selectable marker.

FIG. 2A shows the nucleotide sequence of the entire ORF of S. cerevisiae SSB2 gene (SEQ. ID NO: 1) coding for ribosome associated molecular chaperon; FIG. 2B shows a 1,233 bp fragment of the ORF encoding a cytosol soluble N terminus (411 aa region possessing an ATPase activity (NSSB2) (SEQ. ID NO: 2)

FIG. 10A shows a nucleotide sequences of a complete ORF of the E. coli apy gene coding for apyrase (SEQ ID. NO. 4); 10B shows and a 675 bp fragment of the nucleotide sequence encoding a 224 aa region of the apyrase without the N-terminal periplasma targeting sequence (SEQ ID NO 5); and 10C shows the protein sequence of the 224 aa region of the apyrase (SEQ ID NO 6).

DETAILED DESCRIPTION

Figure 1A:
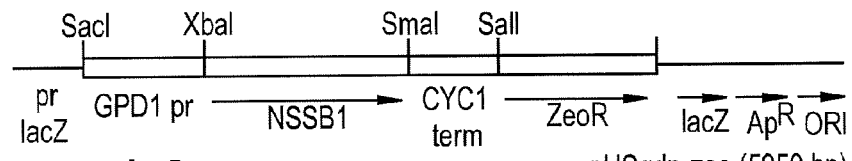

The inventors discovered that lowering the level of ATP yield during growth for alcoholic fermentation in yeast cells can increase ethanol yields and simultaneously drop substrate conversion to biomass. This is accomplished by the construction of yeast strains that yield less ATP during alcoholic fermentation (e.g. one mole ATP, as *Z. mobilis* does in ED pathway) but without transferring the activities of the ED pathway into the yeast. The resulting yeast strains combine all the available advantages of yeast with the high ethanol yield typified by *Z. mobilis*. Two approaches for construction of such yeast strains can be used.

The inventors have discovered that to maintain the ATP level low during yeast alcoholic fermentation through the EMP pathway, it is not necessary to substitute it with the ED pathway activities to lower ATP efficiency. It is possible to maintain the EMP pathway unchanged but to lower the level of ATP by either activation or overexpression of a cytosolic ATPase or an exogenous apyrase, or by introducing agents that induce a futile cycle in the yeast dissipating the cellular pool of ATP.

The present disclosure describes successful lowering of cellular ATP by overexpression of the 5' part of the endogenous *S. cerevisiae* SSB2 gene encoding the cytosolic ATPase domain. The engineered strains showed decreased cellular ATP level during anaerobic and aerobic cultivation and were characterized by reduction in biomass yield and a corresponding increase in ethanol yield during glucose utilization under anaerobic, aerobic or semi anaerobic conditions. Strains were also engineered to overexpress an *E. coli* apyrase, which is an enzyme that cleaves two phosphates from ATP, and some of these co-expressing strains also generated increased ethanol production and decreased biomass accumulations. These approaches are useful for the construction of new generation of industrial strains of *S. cerevisiae* which are characterized by improved ethanol yield from conventional (glucose, sucrose) or other non-conventional carbohydrate based feedstocks (lignocellulose).

Material and Methods used for Exemplary Embodiments

Strains, Plasmids and Growth Conditions.

The *Saccharomyces cerevisiae* strain BY4742 (MATα, his3Δ1, leu2Δ0, lys2Δ0, ura3Δ0; Giaever et al., 2002) was used for expression of the 5' part of the SSB2 ORF coding for the ATPase domain. *Escherichia coli* DH5α (Φ80dlacZΔM15, recA1, endA1, gyrA96, thi-1, hsdR17 (rK-, mK+), supE44, relA1, deoR, Δ(lacZYA-argF) U169) was used for general purposes and routine subcloning.

For plasmid DNA isolation *E. coli* strains were grown in LB media at 37° C. for 18 hours as described (Sambrook and Rusell 2001). *S. cerevisiae* strains were incubated at 30° C. For routine application yeast strains were maintained in rich YPD (0.5% yeast extract, 1% peptone and 2% glucose) or SD (0.67%, yeast nitrogen base without amino acids, DIFCO) media. For ethanol fermentation YPD media or SD media supplemented with 2 or 4% glucose or with 10% galactose were used. When antibiotic selection was needed, strains were incubated with ampicillin (100 μg ml-1), zeocin (25 μg ml-1 for *E. coli* and 150 μg ml-1 for *S. cerevisiae*). When required, histidine (20 mg $L^{-1}$), leucine (60 mg $L^{-1}$), lysine (20 mg $L^{-1}$), or uracil (20 mg $L^{-1}$) were added. The chromogenic substrate X-gal and promoter inducer IPTG (Fermentas, Vilnius, Lithuania) were used according to the manufacturer specifications.

DNA Manipulations.

Genomic DNA from *S. cerevisiae* strains was isolated using the Wizard® Genomic DNA Purification Kit (Promega, Madison, Wis., USA). Plasmid DNA from *E. coli* was isolated using the Wizard® Plus SV Minipreps DNA Purification System (Promega). Taq and High Fidelity polymerase mix, T4 DNA ligase, T4 DNA polymerase and restriction enzymes were used according to recommendation of supplier (Fermentas). *S. cerevisiae* transformation was performed by standard protocol (Sambrook and Rusell 2001).

Construction of Plasmids.

Expression cassette preparation. The GPD1 promoter (the promoter of the GPD1 gene encoding *S. cerevisiae* glycerol-3-phosphate dehydrogenase, Albertyn et al., 1994) was amplified as 874 bp fragment from the chromosome of *S. cerevisiae* BY4742 with GPD1PF (TGAGCTCAGCGTGTAGACGTAGTATAAC) SEQ ID NO: 7; and GPD1PR (TCTAGATCTCTATCAGCAGCAGCAGACAG) SEQ ID NO: 8 primers and T/A cloned into EcoRV site of pBluescriptIISK+. The respective promoter region was retrieved as SacI-XbaI fragments (sites for restriction endonucleases SacI and XbaI are underlined) and cloned into the corresponding site of the pUC57 vector resulting in the pUGPD1P plasmid. The *S. cerevisiae* CYC1 gene terminator region was amplified with CYC1F (ATCCCGGGAAGCCTGTGAGTAAA CAGGC) SEQ ID NO: 9 and CYC1R (TAGTCGACTGTTA CATGCGTACACGCGT) SEQ ID NO: 10 primers from the chromosome of *S. cerevisiae* BY4742 as 234 bp fragment (sites for restriction endonucleases SmaI and SalI are underlined) and cloned into EcoRV site of pBluescriptIISK+, than retrieved as SmaI-SalI fragment and cloned into respective site of pUGPD1P plasmid to yield the pGPD1P construct (the expression cassette is shown in FIG. 1A).

Plasmids for NSSB2 Expression.

Figure 1B:
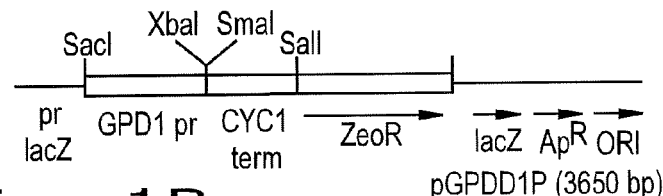

The 1,233 bp fragment of SSB2 ORF coding for 411 N-terminal amino acid residues of SSB2 possessing ATPase activity (NSSB2; FIG. 2) and 12 bp preceding the start codon of the ORF were amplified from the chromosome of *S. cerevisiae* BY4742 with SSB2F (ATCTAGATCCTCATTAACA ATG-GCTGAAGGT) SEQ ID NO: 11 and SSB2R (AT CCCGGGAATTCAACCTTGCATACCAACACC) SEQ ID NO: 12 primers (sites for restriction endonucleases XbaI and SmaI are underlined) and T/A cloned into pUC57. The obtained plasmid was digested with XbaI and SmaI restriction endonucleases and NSSB2 was subcloned into the XbaI-SmaI sites of the pGPD1P expression cassette under control of GPD1 promoter that yielded pUSgpdp. Plasmid pUSgpdp was digested with HindIII, end blunted and the zeocin resistance cassette was cloned into the plasmid to give pUSgpdp-zeo (FIG. 1B). The obtained construct was linearized with SacI and transformed into *S. cerevisiae* BY4742. Transformants were stabilized and the presence of the recombinant construct (NSSB2 under the GPD1 promoter) was verified by a PCR procedure using the forward primer specific to the promoter and the reverse one specific to NSSB2.

Plasmids for Expression of Apy and NSSB1 Under the Control of Galactose-Inducible Promoter.

Figure 1C:
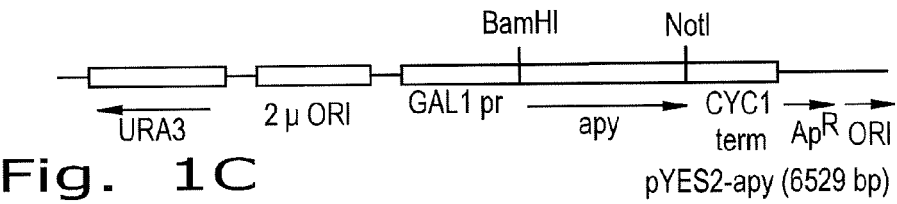
Figure 1D:
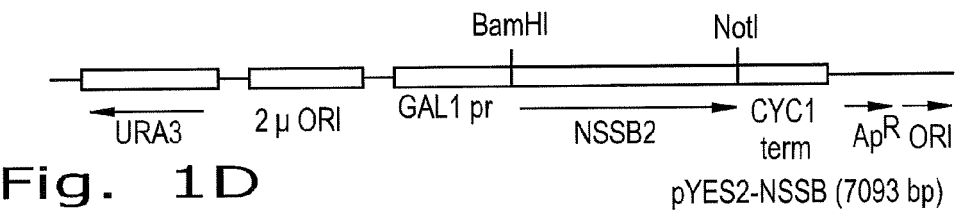
Figure 3A:
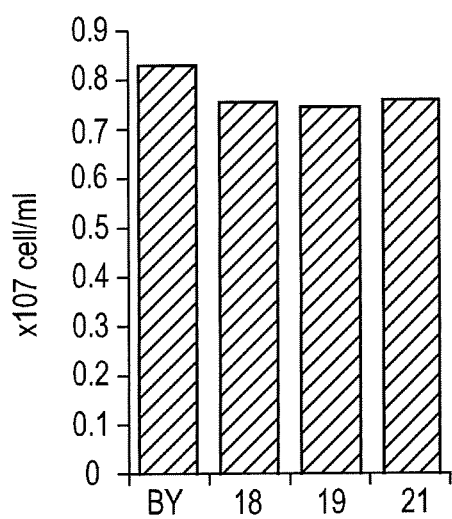
FIG. 3C shows the amino acid sequence encoded by the N-terminus (SEQ ID NO 3).
FIG. 3 shows biomass (3A) and ethanol (3B) accumulation by the recombinant strains of S. cerevisiae harboring NSSB2 driven with the GPD1 promoter after 5 days of growth at anaerobic conditions in 2% glucose supplemented YPD medium. 18, 19, 21—stable recombinant strains. BY—the wild type strain BY4742.
Figure 3B:
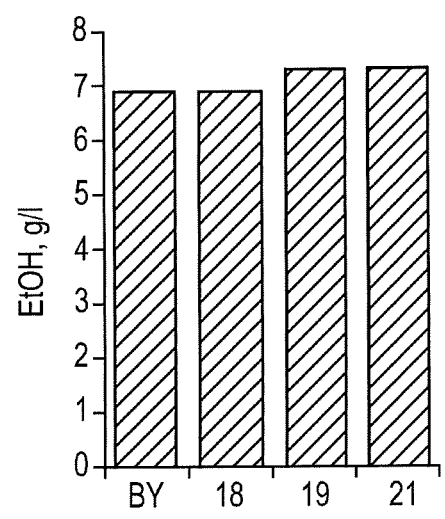

An apyrase gene apy from *E. Coli* strain HN280 was amplified from the virulence plasmid pinv (genbank accession no. AJ315184) (FIG. 3A) omitting the first 70 bp that encode the endogenous N-terminal periplasma targeting sequence with primers Ko390 (CGCGGATCCATG CTGAAGGCAGAAG-GTTTTCTC) SEQ ID NO: 13 and Ko391 (TTT GCGGCCGCTTATGGGGTCAGTTCATTGGTAGGAGTA TTTAATTC) SEQ ID NO: 14 (FIG. 3B). NSSB1 gene in turn was amplified with primers V3f (CGC GGATCCATGGCTGAAGGTGTTTTCCAAGGTG) SEQ ID NO: 15 and Ko389 (TTT GCGGCCGCTCAACCTTGCATACCAACAC) SEQ ID NO: 16 using pusgpdp as a template. Synthesized fragments were double digested with bamhi/noti and ligated with bamhi/noti digested plasmids pyes2 (contains URA3 gene as a selective marker and GAL1 promoter for expression) (Invitrogen). The resulted plasmids were named pyes2-apy (FIG. 1C) and pyes2-NSSB (FIG. 1D).

Selection of Stable Transformants of *S. cerevisiae*.

*S. cerevisiae* transformants were stabilized by alternating cultivation in nonselective and selective media. Transformants that preserved their phenotype (zeocin resistance) provided by the dominant ZeoR marker after this cultivation were considered as stable ones. The presence of desirable construct (NSSB2 under the GPD1 promoter) in the genome of stable transformants were confirmed by PCR. Verification of yeast transformants containing replicative plasmids was performed via plasmid rescue by transformation of *E. coli* with subsequent restriction analysis.

Ethanol Production and Growth Analysis.

Strains were grown overnight in YPD media, washed with sterile water and equal amounts of each culture were inoculated in the test media. For *S. cerevisiae* BY4742 pUSgpdp-zeo+ strains, YPD supplemented with 2 or 4% glucose was used. For anaerobic growth the GENbox system (bioMérieux, Marcy l'Etoile, France) was used. Strains were grown in the rotary shaker Inkubator 1000 Heidolph (Schwabach, Germany) at 28° C. and samples were taken every 24 hours in the case of aerobic conditions and immediately after inoculation and after 5 days of growth in the case of anaerobic growth. For galactose fermentation recombinant strains were grown overnight in SD media An initial biomass concentration for galactose fermentation was 15 µg L$^{-1}$. The efficiency of galactose fermentation of the obtained transformants with plasmid pYES2-apy, pYES2-NSSB and control plasmid pYES2 was evaluated on SD medium supplemented with mixture 1% or 5% glucose and 10% of galactose. Fermentation was carried out under semi-anaerobic (120 revolutions/min) condition during 1-3 days. The biomass was measured by optical density with a spectrophotometer at 600 nm and cell density was calculated. Ethanol and glucose concentrations were measured by protocols described before (Gonchar et al., 2001, Gonchar, 1998).

Assay of ATP and ATPase in Yeast Cells.

ATP assay in yeast cells was performed by a method developed in the inventors' lab as one of several suitable methods available to one of ordinary skill in the art. The method utilizes a preparation of riboflavin kinase obtained from the recombinant *Candida famata* strain that overexpresses the FMN1 gene encoding the kinase. ATP was extracted from tested yeast cells by 5% trichloracetic acid (5 mg of cells, 30 min). The reaction mixture contained (1 ml of total volume): 75 mM phosphate buffer, pH 8.0; 1 mM MgSO4×7H2O; 1 mM riboflavin; 0.25 mg riboflavin kinase (30 mU/mg of protein) and the ATP extract sample. The reaction continued for 30 min at 37° C. and then was stopped by boiling for 5 min. Resultant flavin mononucleotide (FMN) was assayed by fluorometric analysis with Turner Quantech FM 109510-33 fluorometer after chromatographical separation of FMN in 5% Na2HPO4. A blank containing only assay medium was measured for each reaction. A standard calibration curve for ATP was used to calculate the ATP formed.

ATPase activity was measured as described elsewhere (Tashima, 1975) with slight modifications. A reaction mixture contained 50 mM Tris/HCl (pH 7.5), 70 mM KCI, 35 mM NaCI, 2 mM MgCl$_2$, 70 µM CaCI$_2$ and 3 mM ATP. Final concentration of added protein was 0.05 mg ml$^{-1}$. After incubation at 37° C. for 15 min the reaction was stopped with trichloroacetic acid and the phosphate released from ATP was determined by established procedures (Fiske and Subbarow, 1925).

Results

Screening of the *S. Cerevisiae* Genome for Soluble ATPase Gene:

As mentioned herein before, different strategies can be used to control the intracellular ATP level. One first approach is based on the generation of futile cycles that are spending the energy of ATP hydrolysis for reversed metabolic reactions. One of the most studied futile cycles is conversion of fructose-6-phosphate into fructose-1,6-bisphosphate by phosphofructokinase with the use of ATP and its counterpart catalyzed by fructose-1,6-bisphosphatese. While this strategy is indeed be an alternative embodiment of the present invention, is noted that generation of futile reactions will also involve some alteration of biochemical pathways leading to accumulation of ethanol in such way influencing the final level of production. One ordinary skill in the art can readily obtain the sequence encoding the *S. cerevisiae* fructose-1,6-bisphosphatese and engineer it under operable control of the GPD promoter analogously as done here, or use any other *S. cerevisiae* promoter to generate an exemplary embodiment of this practice.

A second approach more fully exemplified herein is based on regulated overexpression of ATP hydrolyzing enzymes: ATPases. Most ATPases are components of heterooligomers and are localized or associated with cell membranes. This feature of this class of enzymes makes their overexpression in the cytosol difficult due to potential toxic effects that can be caused by accumulation of insoluble proteins in the cytoplasmic compartment. To find a more suitable candidate ATPase, the inventors performed a *S. cerevisiae* genome search for genes encoding soluble ATPases. Two genes were chosen as candidates for overexpression. SAP1 encodes a large cytosolic protein with unknown function but displaying features characteristic to ATP hydrolyzing enzymes. SAP1 is predicted to encode a protein of the AAA family (ATPase Associated with different cellular Activities). SAP1 was previously identified by interaction with the *S. cervisiae* chromatin protein Sin1p (Liberzon et al., 1996). Although not exemplified herein, over expression of the SAP1 protein, is another suitable candidate for reducing ATP in yeast.

The exemplified candidate is the ATPase domain of the SSB2 gene coding for ribosome associated molecular chaperon (FIG. 2). The SSB2 protein (SSB2p) is responsible for correct folding of nascent polypeptide chain during its release from the ribosome. The energy of ATP hydrolysis is utilized to stabilize SSB2p complex with nascent protein. The SSB2p consists of three distinct domains. One of them located in the N-terminal 44 kDa region of protein possesses an ATPase activity that is repressed by two other C-terminal domains. The isolated 44 kDa ATPase domain was shown to posses higher affinity to ATP and increased velocity of reaction compared with the full length protein (Pfund et al., 2001). The N-terminal domain of SSB2p protein was therefore chosen to exemplify the methods of the present invention.

A third approach also further exemplified herein that may be expression of ATP-diphosphohydrolases, or apyrases, which are enzymes that hydrolyze both the γ- and β-phosphates of ATP and ADP. They are distinct from other phosphohydrolases with respect to their specific activity, nucleotide substrate specificity, divalent cation requirement, and sensitivity to inhibitors (Plesner, 1995; Handa and Guidotti, 1996). Apyrases are ubiquitously expressed in eukaryotes and have additionally been found in some prokaryotes, indicating a general role for these enzymes across species. Bacterial apyrase apy from *E. coli* was used for decreasing the yeast intracellular ATP level in the present exemplary embodiments, but other pyrases make work as well or better than the E. coli enzyme.

Cloning and Overexpression of 5' Terminal Part of SSB2 Gene Encoding ATPase Domain:

The 1,233 bp fragment of the SSB2 ORF encoding N-terminal 411 amino acid residues of SSB2p protein (herein designated NSSB2) is depicted in FIG. 2B, which, along with the 12 bp preceding start codon of the ORF were amplified by using PCR procedure. The primers were designed in a way to generate a TGA stop codon at the place of GAC encoding aspartate residue. In this way protein synthesis is terminated after 411 codons leading to production of truncated protein with a molecular weight 44 kDa that corresponds to the previously described ATPase domain of SSB2p. The obtained DNA fragment was cloned into pUC57 by T/A cloning and subcloned into the pGPD1P expression cassette as illustrated in FIG. 1A under the control of GPD1 gene promoter. This promoter is known to be constitutively active in yeast and is upregulated under osmotic stress conditions (Albertyn et al., 1994). The zeocin resistance gene was cloned into HindIII site of resultant plasmid to yield pUSgpdp-zeo as depicted in FIG. 1B. The plasmid was introduced into the S. cerevisiae BY4742 strain. Stable zeocin resistant transformants were selected for further study. The presence of the ZeoR gene and NSSB2 under the GPD1 promoter in recombinant strains was verified by PCR with the use of two sets of corresponding primers. Finally, three recombinant strains were selected for further tests.

Growth and Ethanol Accumulation by Recombinant S. Cerevisiae Strains Harboring NSSB2 Under the GPD1 Promoter:

The stains harboring NSSB2 under the control of GPD1 promoter were tested for their ability to grow and produce ethanol. Due to the fact that the selected promoter does not require any additional factors or inducers for its basic functioning, tests were performed at rich YPD medium supplemented with 2 or 4% glucose.

Figure 4A:
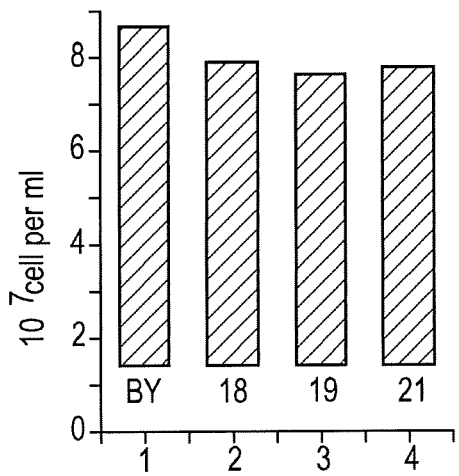
FIG. 4 shows biomass (A) and ethanol (B) accumulation and ethanol to biomass ratio (C) for the S. cerevisiae strains harboring NSSB2 under the GPD1 promoter after 5 days of growth at anaerobic conditions in 4% glucose supplemented YPD medium. 18, 19, 21—stable recombinant strains. BY—the wild type strain BY4742.
Figure 4B:
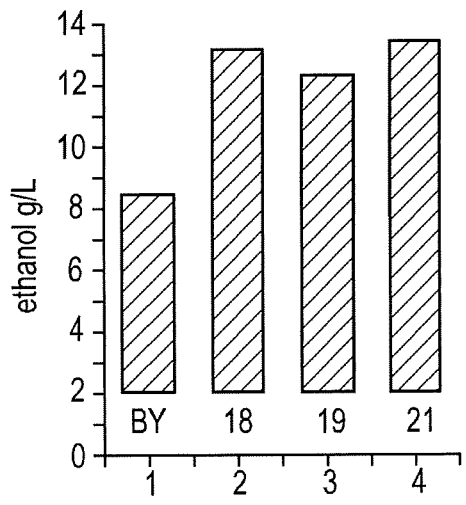
Figure 4C:
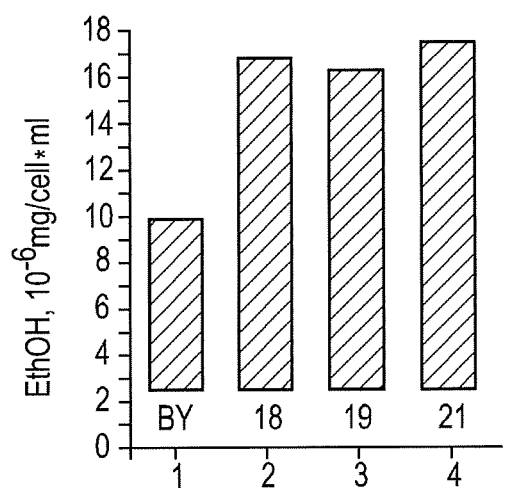

After 5 days of growth under anaerobic conditions in the medium supplemented with 2% glucose the S. cerevisiae strains expressing NSSB2 driven by the GPD1 promoter did not display any difference in ethanol production compared to the wild type strain. The growth of recombinants was slightly decreased 3-5%; (see FIG. 3). However, when the medium was supplemented with 4% glucose, the same strains showed reduction of biomass accumulation (up to 20%) compared to the wild type. In addition, under these conditions we observed an elevated accumulation of ethanol by the recombinant strains. Thus, the final ethanol to biomass ratio was significantly higher for S. cerevisiae pUSgpdp-zeo+ compare to the parental strain (see FIG. 4).

Figure 5:
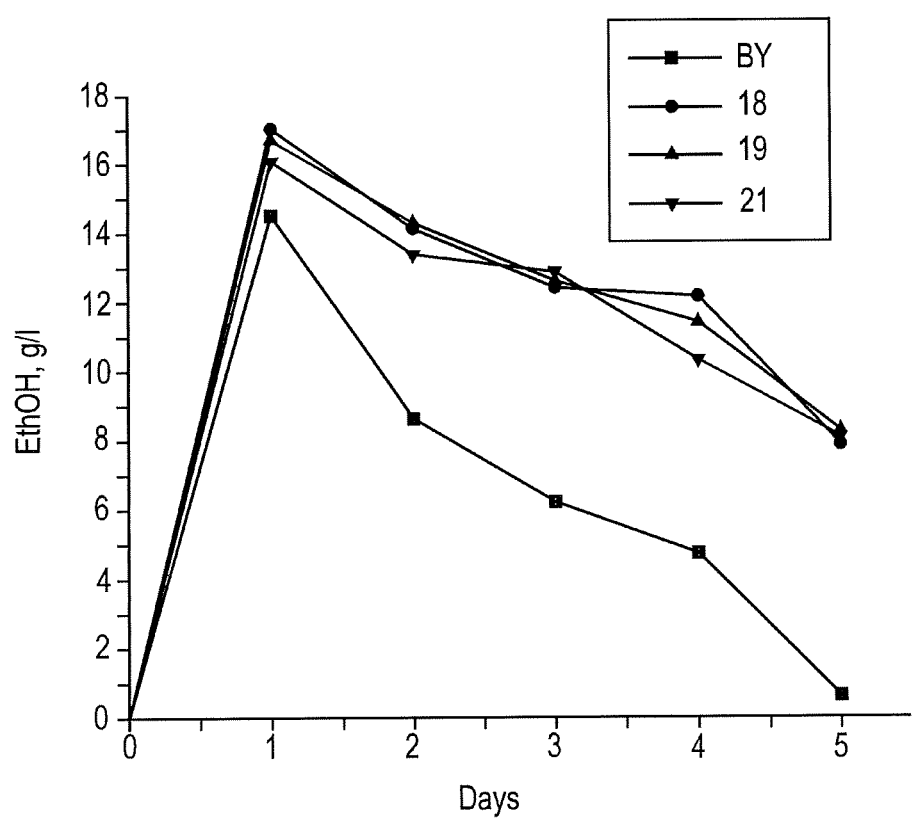
FIG. 5 illustrates dynamics of ethanol accumulation by S. cerevisiae strains harboring NSSB2 driven with the GPD1 promoter at aerobic conditions. 18, 19, 21—stable recombinant strains. BY—the wild type strain BY4742.
Figure 6A:
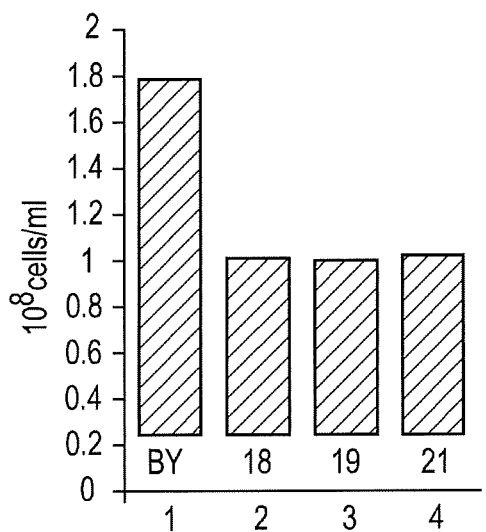
FIG. 6 shows biomass (A) and ethanol (B) accumulation and ethanol to biomass ratio (C) for the strains of S. cerevisiae harboring NSSB2 driven with the GPD1 promoter after 5 days of growth at aerobic conditions in 4% glucose supplemented YPD medium. 18, 19, 21—stable recombinant strains. BY—the wild type strain BY4742.
Figure 6B:
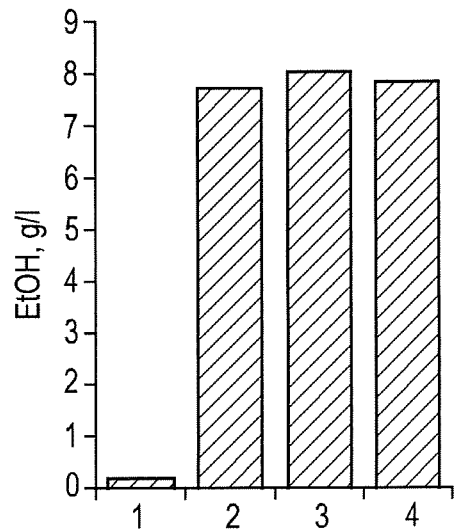
Figure 6C:
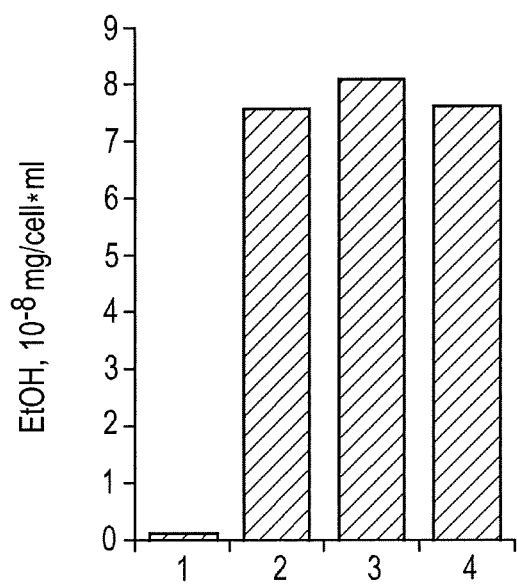

The same experiments were performed under aerobic conditions. The samples were taken every 24 hours and biomass and ethanol concentration were measured. In the case of the wild type strain the maximal level of ethanol production was observed after 24-30 hours of growth and reached 14-15 g per liter (see FIG. 5). During this time almost all glucose was fermented by the tested strains. After that, cells entered an oxidative phase of growth and started to reutilize ethanol from media. Thus, after 5 days of growth in the case of wild type strain the final ethanol concentration was decreased to 0.6-1.2 g per liter (see FIG. 6). In the case of the recombinant strains expressing NSSB2 under the GPD1 promoter the maximum of ethanol accumulation was observed between 24 and 48 hours of growth that coincides with the active fermentation of glucose and biomass augmentation. However, contrary to the wild type strain, the recombinants were not able to reutilize ethanol from medium effectively (see FIG. 5). Thus, even after 5 days of cultivation of the recombinant strains, the ethanol concentration in medium was up to 8-12 g per liter, which was 10 to 12 times higher in comparison to the parental S. cerevisiae BY4742 strain. Notably, the recombinant strains also were characterized by decreased growth. After 48 hours of incubation the growth rate of recombinant strains was depressed and after 5 days of incubation it reached $1-1.2 \times 10^7$ cell per ml, which was two times less than that of BY4742.

ATP was assayed in one of studied recombinant strains. There it was shown that the cells of the recombinant strain #18 after 5 days of incubation under aerobic conditions in 4% glucose supplemented YPD medium contained 2.5 times lower amount of ATP in comparison to the parental BY4742 strain as shown in Table 1.

TABLE 1

Assay of ATP in recombinant strain #18 that expresses the NSSB2 driven with the GPD1 promoter after 5 days of growth at aerobic conditions in 4% glucose supplemented YPD medium.

| Strain | ATP, µmol/g of cells |
|---|---|
| BY4742 | 1.0 |
| #18 | 0.4 |

It is demonstrated that both reduced growth rate and decreased ATP content in the recombinant strains are caused by expression of 5' part of SSB2 gene. It is known that the N-terminal part of SSB2p has strong ATPase activity (Pfund et al., 2001). Recombinant strainsovre expressing NSSB2p grown under aerobic and anaerobic conditions show increased ethanol production. The yeast growth consists of two periods. During the first hours of incubation the glucose is effectively fermented into ethanol with the rapid production of ATP and ethanol accumulation. This ATP is spent for biomass augmentation and also used to initialize the catabolic reactions that lead to reuse of previously produced ethanol. The expression of the ATPase domain of SSB2 is therefore shown to cause a decrease in intracellular ATP level that leads to reduction of growth as well as inhibit the secondary reutilization of accumulated ethanol resulting in increased ethanol production per cell.

Generation and Evaluation of Recombinant S. Cerevisiae Strains Harboring NSSB1 and Ecapy Under Galactose-Inducible Promoter An apyrase gene apy from E. coli lacking N-terminal periplasma targeting sequence was amplified as 675 bp fragment and in parallel with NSSB1 gene of S. cerevisiae was cloned under the control galactose-inducible GAL1 promoter in frame of replicative plasmid pYES2. The resulting plasmids pYES2-apy and pYES2-NSSB were transformed to the recipient BY4742 strain of S. cerevisiae. Transformants were selected on mineral medium lacking uracil and verified via plasmid rescue by transformation of E. coli. The growth kinetics, ethanol synthesis, ATPase activity of obtained recombinant strains were analyzed under conditions of transcriptional activation of target genes.

Figure 7A:
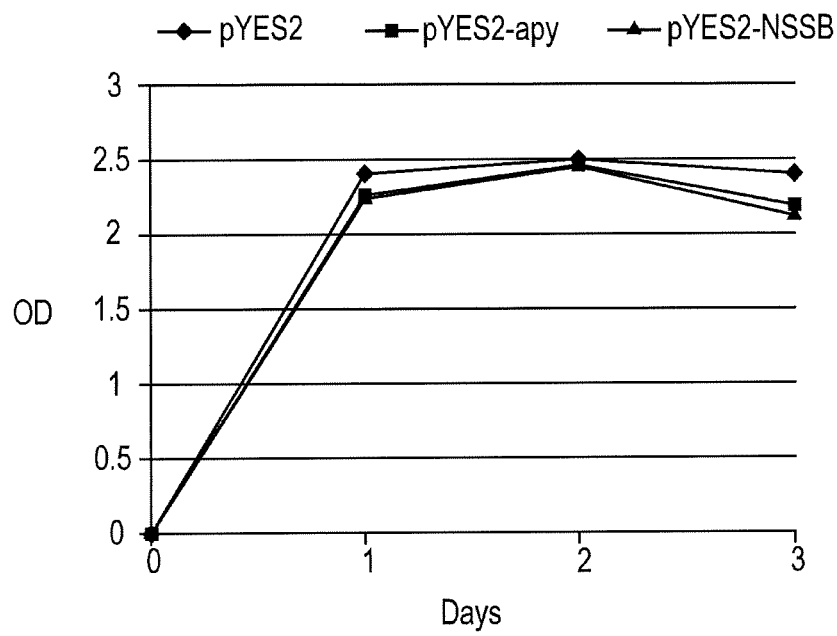
FIG. 7 shows kinetics of biomass accumulation for the S. cerevisiae transformants with plasmids pYES2 (control), pYES2-apy (harboring apy gene driven with the GAL1 promoter) and pYES2-NSSB (harboring NSSB1 driven with the GAL1 promoter) under semi-anaerobic conditions in SD medium supplemented with 1% glucose+10% galactose (A) or 5% glucose+10% galactose (B).
Figure 7B:
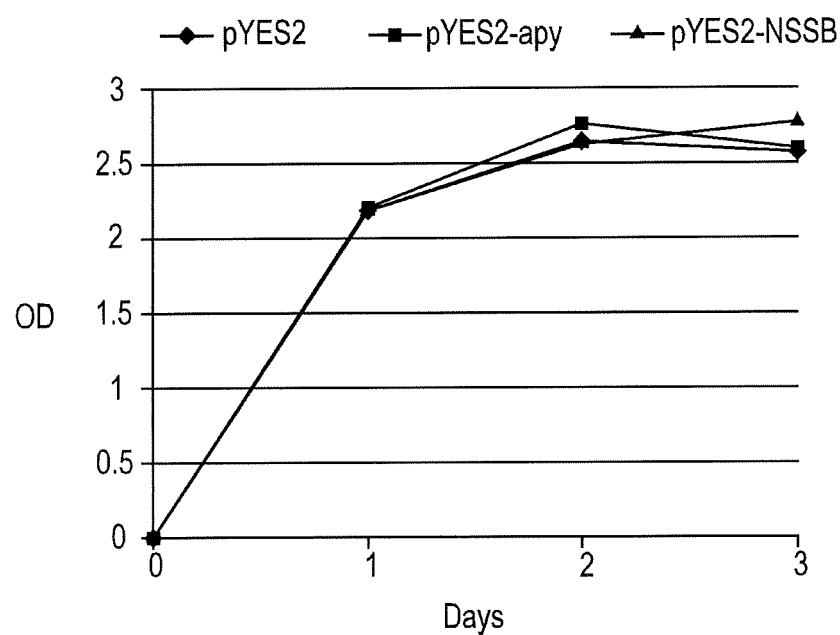

The growth kinetic of S. cerevisiae transformants with plasmids pYES2-apy and pYES2-NSSB was analyzed on the galactose containing media (1% glucose+10% galactose and 5% glucose+10% galactose) in 50 ml Erlenmeyer flasks in 20 ml of defined media. Initial biomass concentration was 15 mg $L^{-1}$. Transformants were characterized by slight growth retardation during cultivation on media containing 1% glucose+10% galactose (FIG. 7A). However no significance difference in growth was revealed during cultivation on medium containing 5% glucose+10% galactose (FIG. 7B). Apparently a higher glucose concentration in the medium represses expression of target genes.

Figure 8A:
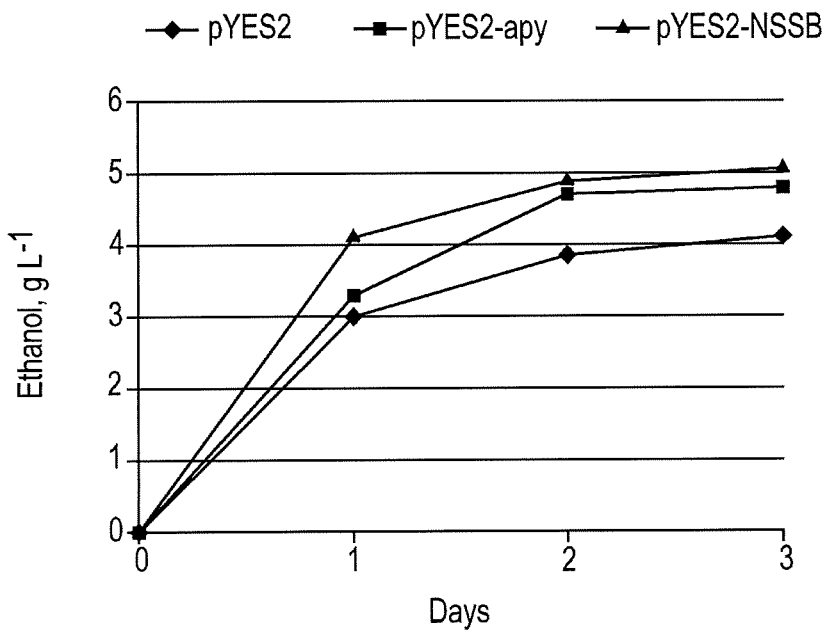
FIG. 8 illustrates Ethanol accumulation for the S. cervisiae transformants with plasmids pYES2 (control), pYES2-apy (harboring apy gene driven with the GAL1 promoter) and pYES2-NSSB (harboring NSSB 1 driven with the GAL1 promoter) under semi-anaerobic conditions in SD medium supplemented with 1% glucose+10% galactose (A) or 5% glucose+10% galactose (B).
Figure 8B:
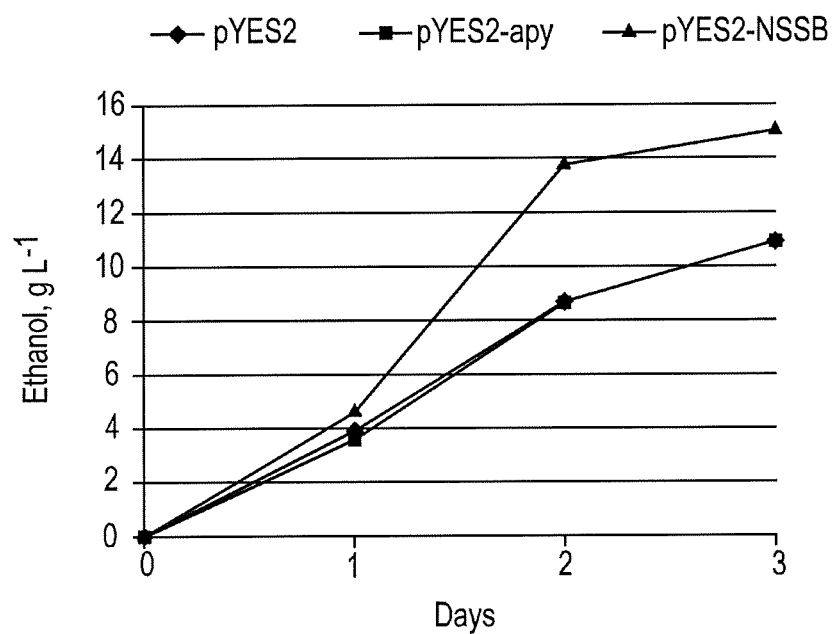
Figure 9A:
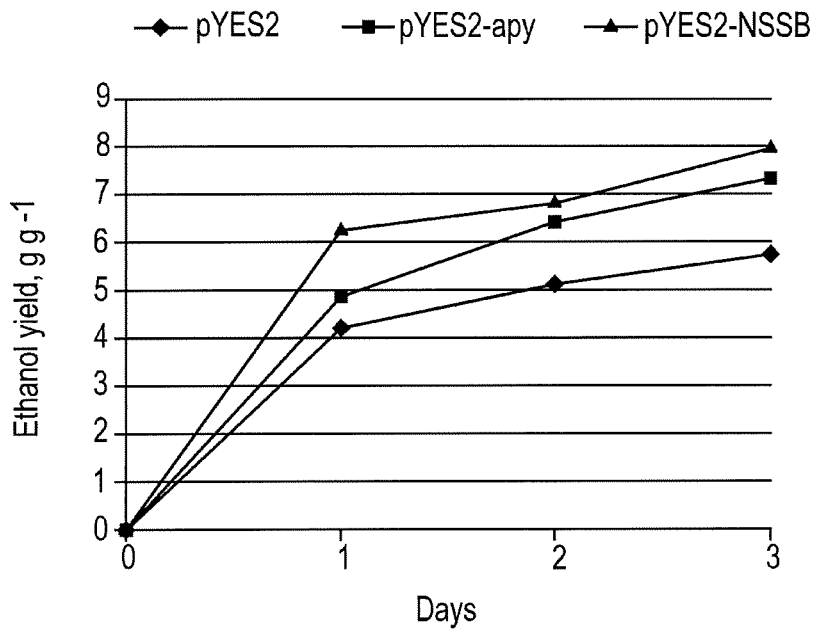
FIG. 9 illustrates ethanol yield for the S. cerevisiae transformants with plasmids pYES2 (control), pYES2-apy (harboring apy gene driven with the GAL1 promoter) and pYES2-NSSB (harboring NSSB 1 driven with the GAL1 promoter) under semi-anaerobic conditions in SD medium supplemented with 1% glucose+10% galactose (A) or 5% glucose+10% galactose (B).
Figure 9B:
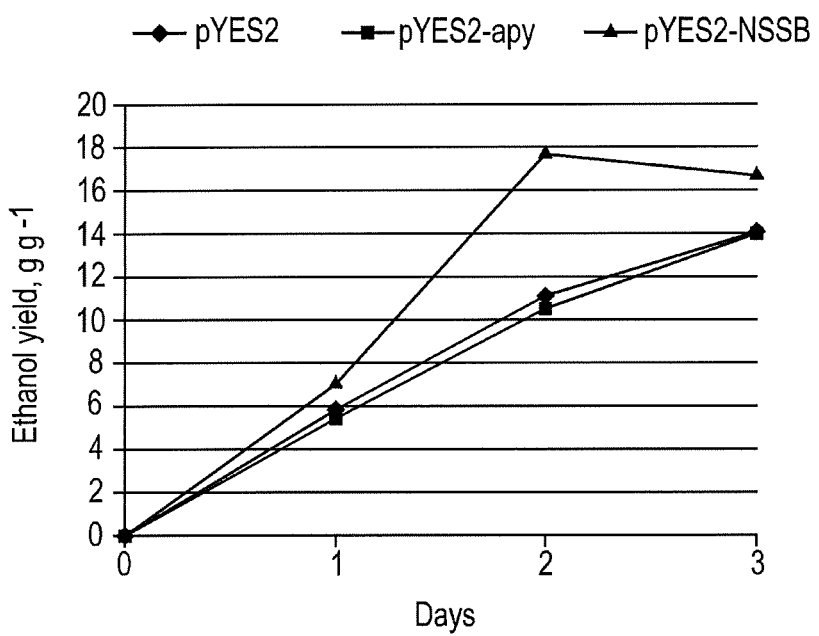

The efficiency of galactose fermentation of the obtained transformants with plasmid pYES2-apy, pYES2-NSSB and control plasmid pYES2 was evaluated under these conditions. Despite the total low amount of synthesized ethanol, the increase in alcoholic fermentation and ethanol yield of selected transformants was shown on media containing 1% glucose+10% galactose (FIG. 8A, 9A). Ethanol accumulation and yield of the transformant with pYES2-NSSB on the third day of fermentation was highest and was 22% and 39% increase in that order as compared to the parental strain (Table 2). The transformant with pYES2-apy showed 17% and 28% increase of ethanol accumulation and yield as compared with the control strain (Table 2). The efficiency of alcoholic galactose fermentation was also measured on medium containing mixture of sugars 5% glucose+10% galactose. The increase of ethanol accumulation and yield was reached only for the transformants harboring pYES2-NSSB while the transformant with pYES2-apy synthesize ethanol as the control strain (FIG. 8B, 9B). The transformant harboring pYES2-NSSB displayed 37% and 17% increase of ethanol accumulation and yield as compared with the control strain (Table 2), while the ATPase specific activity was higher only in the transformant with pYES2-NSSB (transformant with highest level of ethanol production) (Table 2).

TABLE 2

Ethanol synthesis, yield and specific ATPase activity of S. cerevisiae transformants and control strain on the third day of fermentation.

| Strain | 1% glucose + 10% galactose | | 5% glucose + 10% galactose | | ATPase, U/mg |
|---|---|---|---|---|---|
| | Ethanol, g L$^{-1}$ | Ethanol, g g$^{-1}$ of biomass | Ethanol, g L$^{-1}$ | Ethanol, g g$^{-1}$ of biomass | |
| BY4742/ pYES2 | 4.11 | 5.73 | 10.95 | 14.26 | 0.66 |
| BY4742/ pYES2-apy | 4.8 (+17%) | 7.34 (+28%) | 10.95 | 14.1 | 0.80 |
| BY4742/ pYES2-NSSB | 5.03 (+22%) | 7.94 (+39%) | 15 (+37%) | 16.7 (+17%) | 0.53 |

Thus, constructs with the GAL1 promoter confirmed earlier obtained proof of the concept, i.e. that induction of SSB1-encoding ATPase, even under this promoter induced by galactose led to substantial increase in ethanol yield. Unfortunately, this promoter is not very convenient as is strongly repressed by glucose.

The present application cites several references, summarized herein below. Each such citation is to aid one of ordinary skill in the art in better understanding the present invention and to find sources of sequences, recombinant techniques, tests and other routine information that would enable one of ordinary skill to practice any of numerous embodiments of the present invention. Accordingly, each reference cited is incorporated herein in it's entirety by reference, excepting such parts of if such references that contain information that conflicts with the information taught herein, in which case the present disclosure shall be deemed controlling over the incorporated reference

REFERENCES

Albertyn J., Hohmann S., Thevelein J. M., Prior B. A. (1994) GPD1, which encodes glycerol-3-phosphate dehydrogenase, is essential for growth under osmotic stress in Saccharomyces cerevisiae, and its expression is regulated by the high-osmolarity glycerol response pathway. Mol Cell Biol. 14:4135-4144.

Bai F. W., Anderson W. A., Moo-Young M. (2008) Ethanol fermentation technologies from sugar and starch feedstocks. Biotechnology Advances 26:89-105.

Fiske C. H., and Subbarow Y. (1925). The colorimetric determination of phosphorus. J. Biol. Chem. 66:375-400.

Giaever G., Chu A. M., Ni L., Connelly C., Riles L., Veronneau S., Dow S., Lucau-Danila A., Anderson K., André B., Arkin A. P., Astromoff A., El-Bakkoury M., Bangham R., Benito R., Brachat S., Campanaro S., Curtiss M., Davis K., Deutschbauer A., Entian K. D., Flaherty P., Foury F., Garfinkel D. J., Gerstein M., Gotte D., Güldener U., Hegemann J. H., Hempel S., Herman Z., Jaramillo D. F., Kelly D. E., Kelly S. L., Kotter P., LaBonte D., Lamb D. C., Lan N., Liang H., Liao H., Liu L., Luo C., Lussier M., Mao R., Menard P., Ooi S. L., Revuelta J. L., Roberts C. J., Rose M., Ross-Macdonald P., Scherens B., Schimmack G., Shafer B., Shoemaker D. D., Sookhai-Mahadeo S., Storms R. K., Strathern J. N., Valle G., Voet M., Volckaert G., Wang C. Y., Ward T. R., Wilhelmy J., Winzeler E. A., Yang Y., Yen G., Youngman E., Yu K., Bussey H., Boeke J. D., Snyder M., Philippsen P., Davis R. W., Johnston M. (2002) Functional profiling of the Saccharomyces cerevisiae genome. Nature 418: 387-391.

Gonchar M. V. (1998) Sensitive method for quantitative determination of hydrogen peroxide and oxidase substrates in biological samples. Ukr. Biokhim. Zh. 70:157-163.

Gonchar M. V., Maidan M. M., Pavlishko H. M., Sibirny A. A. (2001) A new oxidase-peroxidase kit for ethanol assays in alcoholic beverages. Food Technol. Biotechnol. 39:37-42.

Hahn-Hagerdal B., Karhumaa K., Jeppsson M., Gorwa-Grauslund M. F. (2007) Metabolic Engineering for Pentose Utilization in Saccharomyces cerevisiae. Adv. Biochem. Engin. Biotechnol. 108:147-177.

Handa M., Guidotti G. (1996) Purification and cloning of a soluble ATPdiphosphohydrolase (apyrase) from potato tubers (Solanum tuberosum). Biochem. Biophys. Res. Commun. 218: 916-923.

Ingledew W. M. Alcohol production by Saccharomyces cerevisiae: a yeast primer, in the alcohol textbook. 3rd ed. UK: Nottingham University Press; 1999.

Jeffries T. W. (2005) Ethanol fermentation on the move. Nature 23:40-41.

Jeffries T. W., Jin Y.-S. (2004) Metabolic engineering for improved fermentation of pentoses by yeasts. Appl. Microbiol. Biotechnol. 63: 495-509.

Lancashire W. E., Dickinson J. R., Malloch R. A. (1998) DNA encoding enzymes of the glycolytic pathway for use in alcohol producing yeast. U.S. Pat. No. 5,786,186.

Leskovac, V., Trivic S., Peric D. (2002) The three zinc-containing alcohol dehydrogenases from baker's yeast, Saccharomyces cerevisiae. FEMS Yeast Res., 2:481-494.

Liberzon A., Shpungin S., Bangio H., Yona E., Katcoff D. J. (1996) Association of yeast SAP 1, a novel member of the 'AAA' ATPase family of proteins, with the chromatin protein SIN1. FEBS Lett. 388:5-10.

Panesar P. S., Marwaha S. S., Kennedy J. F. (2006) Zymomonas mobilis: an alternative ethanol producer. J. Chem. Technol. Biotechnol. 81:623-635.

Pfund C, Huang P, Lopez-Hoyo N, Craig E. A. 2001. Divergent functional properties of the ribosome-associated molecular chaperone Ssb compared with other Hsp70s. Mol. Biol. Cell. 12, 3773-3782.

Plesner L. (1995) Ecto-ATPases: identities and functions. Int. Rev. Cytol. 158: 141-214.

Sambrook J. and Russell D. W. (2001) Molecular cloning: a laboratory manual. 3rd edition. Cold Spring Harbor Laboratory Press, Cold Spring Harbor, N.Y.

Schubert C. (2006) Can biofuels finally take center stage? Nature Biotechnol., 24:777-784.

Sprenger G. A. (1996) Carbohydrate metabolism in *Zymomonas mobilis*: a catabolic highway with some scenic routes. FEMS Microbiol. Lett. 145:301-307.

Tashima Y. (1975) Removal of protein interference in Fiske-Subbarow method by sodium dodecyl sulphate Anal Biochem 69:410-414.

What is claimed is:

1. A yeast strain comprising a recombinant nucleic acid consisting of the nucleic acid sequence as set forth in SEQ ID NO: 5, wherein said recombinant nucleic acid is operably linked to a promoter for overexpression and encodes a cytosol soluble *E. coli* apyrase.

2. The yeast strain of claim 1 further comprising a recombinant nucleic acid encoding a cytosol soluble ATPase, which is operably linked to a promoter for overexpression.

3. The yeast strain of claim 2 wherein the nucleic acid encoding the cytosol soluble ATPase encodes a cytosol soluble N-terminal portion of a *S. cerevisiae* SSB2 protein.

4. The yeast strain of claim 3 wherein the cytosol soluble N-terminal portion of the *S. cerevisiae* SSB2 protein is according to SEQ ID NO: 3.

5. The yeast strain of claim 4 wherein the nucleic acid encoding the N-terminal portion of the *S. cerevisiae* SSB2 protein is according to SEQ ID NO: 2.

6. The yeast strain of claim 1 wherein the *E. coli* apyrase is according to SEQ ID NO: 6.

7. The yeast strain of claim 1 wherein the yeast strain is *S. cerevisiae*.

8. The yeast strain of claim 1 used in A method of enhancing ethanol production by yeast fermentation comprising, growing the recombinant yeast strain of claim 1 on a carbohydrate source under conditions where the carbohydrate source is fermented to make ethanol, wherein an amount of ethanol made in by the recombinant yeast strain under the growth conditions is greater than the amount of ethanol made in a parent of the recombinant yeast strain that lacks the recombinant nucleic acid overexpressing the apyrase.

9. The method according to claim 8, wherein growing the yeast is performed under aerobic conditions.

10. The method according to claim 8, wherein growing the yeast is performed under anaerobic conditions.

11. The method according to claim 8, wherein growing the yeast is performed under aerobic conditions for a first period of time and then under anaerobic conditions for a second period of time, and wherein the enhanced ethanol production occurs under the anaerobic growth conditions.

12. The yeast strain of claim 2 used in A method of enhancing ethanol production by yeast fermentation comprising, growing the recombinant yeast strain of claim 2 on a carbohydrate source under conditions where the carbohydrate source is fermented to make ethanol, wherein an amount of ethanol made in by the recombinant yeast strain under the growth conditions is greater than the amount of ethanol made in a parent of the recombinant yeast strain that lacks the recombinant nucleic acid overexpressing the apyrase and cytosol soluble ATPase.

13. The method according to claim 12, wherein growing the yeast is performed under aerobic conditions.

14. The method according to claim 12, wherein growing the yeast is performed under anaerobic conditions.

15. The method according to claim 12, wherein growing the yeast is performed under aerobic conditions for a first period of time and then under anaerobic conditions for a second period of time, and wherein the enhanced ethanol production occurs under the anaerobic growth conditions.

* * * * *

UNITED STATES PATENT AND TRADEMARK OFFICE
CERTIFICATE OF CORRECTION

PATENT NO. : 8,507,217 B2
APPLICATION NO. : 13/376405
DATED : August 13, 2013
INVENTOR(S) : Dmytruk et al.

Page 1 of 1

It is certified that error appears in the above-identified patent and that said Letters Patent is hereby corrected as shown below:

Title Page, Item (75) Inventor is corrected to read:
-- Kostyantyn V. Dmytruk, Lviv (UA);
Marta V. Semkiv, Lviv (UA);
Andriy Sibirny, Lviv (UA);
Charles Abbas, Champaign (IL) --.

Signed and Sealed this
Sixth Day of October, 2015

Michelle K. Lee
*Director of the United States Patent and Trademark Office*